(12) United States Patent
Yoshida et al.

(10) Patent No.: US 7,851,771 B2
(45) Date of Patent: Dec. 14, 2010

(54) METHOD OF CONSTRUCTING CHIMERIC PLANT BY HEAVY-ION BEAM IRRADIATION

(75) Inventors: Shigeo Yoshida, Wako (JP); Tomoko Abe, Wako (JP); Yasushige Yano, Wako (JP); Nobuhisa Fukunishi, Wako (JP); Ken-ichi Suzuki, Wako (JP)

(73) Assignee: Riken, Wako-shi (JP)

( * ) Notice: Subject to any disclaimer, the term of this patent is extended or adjusted under 35 U.S.C. 154(b) by 1230 days.

(21) Appl. No.: 10/499,808

(22) PCT Filed: Jul. 23, 2002

(86) PCT No.: PCT/JP02/07417

§ 371 (c)(1), (2), (4) Date: Jun. 22, 2004

(87) PCT Pub. No.: WO03/056905

PCT Pub. Date: Jul. 17, 2003

(65) Prior Publication Data

US 2005/0077481 A1     Apr. 14, 2005

(30) Foreign Application Priority Data

Jan. 8, 2002 (JP) ................................... 2002-993

(51) Int. Cl.
G21G 5/00 (2006.01)
C12N 15/82 (2006.01)
C12N 15/01 (2006.01)
C12N 15/00 (2006.01)

(52) U.S. Cl. .................... 250/492.1; 435/468; 435/447; 435/440

(58) Field of Classification Search .................. 800/300
See application file for complete search history.

(56) References Cited

FOREIGN PATENT DOCUMENTS

| JP | 54-49828 A | 4/1979 |
|---|---|---|
| JP | 54-49832 A | 4/1979 |
| JP | 9-28220 A | 2/1997 |
| JP | 10-127195 A | 5/1998 |
| JP | 2002-125496 A | 5/2002 |

OTHER PUBLICATIONS

Chang-Hyu Bae et al. Characterization of a periclinal chimera variegated tobacco (*Nicotiana tabacum* L.) Plant Science 151 (2000) p. 93-101.*
Smith. Plant Tissue Culture. Techniques and Experiments. 2000 Academic Press.*
Pierik R.L.M. In Vitro Culture of Higher Plants Kluwer Academic Publishers 1997. pp. 275-276, 291-296.*
Taylor A, Steeves et al. Patterns in plant development second edition 1991 Cambridge University Press. p. 140.*
Regeneration of chlorophyll chimeras from leaf explants of *Nicotiana tabacum* L. Z. Opatrný1, 2 and Z. Landa1, 3 Biologic Plantarum vol. 16 No. 4 Jul. 1974 p. 312.*
International Preliminary Examination Report issued in corresponding PCT Application No. PCT/JP2003/007417.
Office Action dated May 2, 2005 issued in corresponding Japanese Appl. No. 2002-000993 with English translation.
Nagatomi, Shigeki "Characteristics of chrysanthemum mutants regenerated from in vitro explants irradiated with 12C5+ ion beam"; 23rd Japan Radioisotopes and Radiation Forum Collected papers; Japan Atomic Industrial Forum, Inc. (pp. 366-374); Dec. 8, 1998. (English Abstract).
Canadian Office Action issued in Canadian Patent Application No. 2,472,202 on Nov. 24, 2009.
Nagatomi et al., "Chrysanthemum Mutants Regenerated from in vitro Explants Irradiated with 12C5+ Ion Beam", Institute of Radiation Breeding, Technical News, No. 60 (1997) ISSN 0285-1962 with partial English Translation.

* cited by examiner

*Primary Examiner*—Annette H Para
(74) *Attorney, Agent, or Firm*—Birch, Stewart, Kolasch & Birch, LLP.

(57) ABSTRACT

Petunia explants are irradiated with heavy-ion beams, and the chimeric individuals differentiated from the explants are selected (FSRP method). Then, explants are obtained from the chimeric individuals and subjected to tissue culture, followed by selection of re-differentiated chimeric individuals with stable characters (SSRP method). By these procedures, it becomes possible to create chimeric plants such as variegated petunia efficiently.

5 Claims, No Drawings

METHOD OF CONSTRUCTING CHIMERIC PLANT BY HEAVY-ION BEAM IRRADIATION

TECHNICAL FIELD

The present invention relates to a method of creating chimeric plants, such as variegated petunia, by heavy-ion beam irradiation.

BACKGROUND ART

Petunia is one of the important floricultural products which have been bred and used from old times. Recently, petunia varieties exhibiting various grass types have been developed. Surfinia series developed jointly by Suntory Ltd. and Keisei Rose Nurseries, Inc. are prostrate petunia growing vigorously and flowering from spring to autumn; they are especially popular among a great number of petunia varieties.

Normally, the color of plant leaves is uniformly green. However, there are some plants in which a part of their leaves has a regular or irregular pattern of such a color as yellow, white, or red. Generally, they are called variegated plants and their beautiful appearances have been highly prized from old times. Variegated plants are generated by various causes, and some are generated by chimerism (periclinal chimerism, sectorial chimerism). In petunia, variegated varieties are also known (e.g. limelight, passion variegate, etc.) but the number of such varieties is rather limited.

If means to efficiently create chimeric petunia can be established, it will become possible to obtain a large quantity of petunia varieties, such as variegated varieties, with high commercial value. Such technology is applicable to plants other than petunia.

Under such technical background, the present invention has been made. It is an object of the invention to provide means to create plants with high commercial value, such as variegated petunia, efficiently.

DISCLOSURE OF THE INVENTION

As a result of extensive and intensive researches toward the solution of the above-described problem, the present inventors have found that chimeric mature individual can be obtained efficiently by selecting chimeric individuals at aseptic culture stage, and by collecting explants from the chimeric shoots selected at aseptic culture stage and again selecting chimeric individuals from the shoots formed from the explants. Thus, the present invention has been achieved.

The first invention of the present invention relates to a method of creating a chimeric plant comprising the following steps (1) to (4):

(1) a step of irradiating a plant explant with heavy-ion beams;

(2) a step of allowing the formation of shoots from the explant irradiated with heavy-ion beams;

(3) a step of selecting chimeric shoots from the formed shoots; and (4) a step of growing the selected shoots and obtaining mature plants.

The second invention of the present invention relates to a method of creating a chimeric plant comprising the following steps (1) to (7):

(1) a step of irradiating a plant explant with heavy-ion beams;

(2) a step of allowing the formation of shoots from the explant irradiated with heavy-ion beams;

(3) a step of selecting chimeric shoots from the formed shoots;

(4) a step of collecting explants from the selected shoots;

(5) a step of allowing the regeneration of the collected explants and the formation of shoots therefrom;

(6) a step of selecting chimeric shoots from the resultant regenerated shoots; and (7) a step of growing the selected shoots and obtaining mature plants.

Hereinafter, the first invention described above is referred to as the "FSRP (First Screening of Regenerated Plants) method" and the second invention described above as the "SSRP (Second Screening of Regenerated Plants) method".

Hereinbelow, the present invention will be described in detail.

FSRP method comprises the following steps (1) to (4).

In step (1), a plant explant is irradiated with heavy-ion beams.

The plant used in the invention is not particularly limited. For example, petunia may be used. As petunia, any petunia may be used as long as it belongs to the genus Petunia. For example, commercial varieties such as Surfinia may be used. Plants other than petunia, such as torenia, orchid or dahlia, may also be used.

As the explant, any section may be used as long as it is capable of regeneration. Preferably, a section including a portion which can grow into a bud (e.g. a stem section including an axillary bud) may be used.

As the heavy-ion beams, C ion beams, N ion beams or Ne ion beams of more than 15 MeV per nucleon may be used, for example. The dose is not particularly limited as long as it does not give damage to the explant and falls within the range that allows the generation of chimeric shoots. Preferably, C ion beams of 135 MeV per nucleon are applied in the range from 5 to 50 Gray; N ion beams of 135 MeV per nucleon are applied in the range from 5 to 50 Gray; and Ne ion beams of 135 MeV per nucleon are applied in the range from 1 to 20 Gray.

In step (2), shoots are formed from the explant irradiated with heavy-ion beams.

The formation of shoots may be achieved in accordance with conventional methods (e.g. the explant is placed on MS agar medium or the like, and cultured for several months).

In step (3), chimeric shoots are selected from the thus formed shoots. The chimeric shoots to be selected may be any chimeric shoots. However, those which have high commercial value as garden crops are selected preferably. For example, variegated shoots are preferable. The selection method is not particularly limited. For example, shoots are selected by observation of their appearances. At this time, it is desirable to select not only those shoots which can be confirmed completely chimeric but also those shoots which are suspicious of being chimeric. For example, when variegated shoots are selected, it is desirable to select not only those shoots which have clear spots but also those shoots which have a lighter color in their leaves or flowers, or which are albino.

In step (4), the selected shoots are grown to thereby obtain mature plants. The selected shoots are composed of normal cells and abnormal cells which were generated as a result of the heavy-ion beam irradiation. Generally, such abnormal cells have less survival ability than normal cells, and they may disappear in the course of growth of plants. For this reason, it is observed quite often that an individual which was chimeric at the stage of shoot turns into a normal individual when grown up. Therefore, during the process of growing chimeric shoots into mature individuals, it is desirable to grow them in environments where abnormal cells are easy to survive and propagate as much as possible. In the case of variegated shoots, for example, it is desirable to grow then under weak light conditions (specifically, approx. 100 µmolm$^{-2}$s$^{-1}$ or less) since abnormal cells (i.e. cells constituting spots) are weak in light.

SSRP method comprises the following steps (1) to (7).

(1) a step of irradiating a plant explant with heavy-ion beams;

(2) a step of allowing the formation of shoots from the explant irradiated with heavy-ion beams;

(3) a step of selecting chimeric shoots from the formed shoots;

(4) a step of collecting explants from the selected shoots;

(5) a step of allowing the regeneration of the collected explants and the formation of shoots therefrom;

(6) a step of selecting chimeric shoots from the resultant regenerated shoots; and (7) a step of growing the selected shoots and obtaining mature plants.

The above steps (1) to (7) may be performed in the same manner as in the individual steps of FSRP method. However, the explants collected in step (4) are preferably leaf explants rather than stem explants inducing axillary buds.

Unlike FSRP method in which selected chimeric shoots themselves are grown, SSRP method is characterized by collecting explants from the selected chimeric shoots and again allowing the formation of shoots from those explants. In FSRP method and the conventional selection method, the characters of the selected chimeric individual are not stable, and the chimeric characters may disappear in the course of growth. The regeneration ability of chimeric plants derived from explants collected from shoots with such unstable chimeric characters is weak. Therefore, by selecting chimeric shoots twice as performed in SSRP method, it is possible to exclude chimeric individuals with unstable characters and to select chimeric individuals with stable characters efficiently.

BEST MODES FOR CARRYING OUT THE INVENTION

Example 1

Creation of Variegated Petunia

Sections of stems containing axillary buds were prepared from aseptic plants of the 12 varieties of petunia "Surfinia" shown in Table 1 below. For each variety, 150 sections (3 irradiation doses each consisting of 50 sections were provided) were placed on MS agar medium.

TABLE 1

| Variety (Suntory Ltd.) |
| --- |
| Pink Mini |
| Pink Vein |
| Bride Pink Mini |
| Hot Pink |
| Pastel Pink |
| Violet |
| Violet Mini |
| Blue Vein |
| Large Blue Vein |

TABLE 1-continued

| Variety (Suntory Ltd.) |
| --- |
| Purple |
| Purple Mini |
| White |

Conventional Selection Method: The stem sections placed on the medium were irradiated with $^{12}$C ion beams (5 Gray), $^{14}$N ion beams (5 Gray) or $^{20}$Ne ion beams (1 Gray) of 135 MeV per nucleon at RIKEN Accelerator Research Facilities (RARF). After the irradiation, the stem sections were cultured on MS agar medium for one to three months to allow shoot formation. The regenerated shoots were subjected to rooting under acclimatization conditions and then grown in greenhouse or the like. Subsequently, variegated plants were selected.

FSRP Method: The stem sections placed on the medium were irradiated with $^{12}$C ion beams (5 Gray), $^{14}$N ion beams (5 Gray) or $^{20}$Ne ion beams (1 Gray) of 135 MeV per nucleon at RARF. After the irradiation, the stem sections were cultured on MS agar medium for one to three months to allow shoot formation. The appearances of the formed shoots were observed, and the frequencies of variegated plants were examined. The results are shown in Table 2 below. It should be noted that the variegated plants included not only those individuals in which complete spots were confirmed but also those plants which had a light green color in their entire leaves.

TABLE 2

| | $^{12}$C-ion beams | $^{14}$N-ion beams | $^{20}$Ne-ion beams |
| --- | --- | --- | --- |
| Frequency of Variegated Plants | 19.3% | 25.6% | 9.7% |
| Survival Ratio | 89.7% | 93.4% | 93.2% |

Survival Ratio: Plants from which shoots were formed/Plants irradiated with heavy-ion beams
Frequency of variegated plants: Variegated plants/Regenerated plants As shown in Table 2, variegated plants appeared at a high frequency when any of the three kinds of heavy-ion beams was used. However, these variegated shoots were not stable in their chimeric characters. Chimeric characters disappeared afterward, and only one line out of the 12 varieties retained variegated mutants.

SSRP Method: One line was selected from variegated plants of each of the 12 varieties. Seven leaf disks were prepared from each line and placed on MS agar medium containing 1 mg/L BA and 0.1 mg/L NAA, for regeneration of shoots. Fifty to one hundred individuals of shoots were obtained from one line; although most of them were normal (green) or albino shoots, three mutants of variegated shoots were obtained. The thus obtained variegated mutants were stable in their characters. Each of them was subjected to rooting under acclimatization conditions to thereby obtain a variegated mature plant.

The numbers of variegated mature mutants obtained by the conventional selection method, FSRP method and SSRP method, respectively, are shown in Table 3 below.

TABLE 3

|  | $^{12}C$ ion beams | $^{14}N$ ion beams | $^{20}Ne$ ion beams | Total |
| --- | --- | --- | --- | --- |
| Conventional Selection Method | 0 | 0 | 0 | 0 |
| FSRP Method | 0 | 1 | 0 | 1 |
| SSRP Method | 1 | 1 | 1 | 3 |

As shown in Table 3, no variegated mutants were obtained in the conventional method in which variegated plants are selected in greenhouse. In contrast with this, variegated mutants were obtained by either FSRP or SSRP method in which variegated plants are selected at aseptic culture stage. More variegated mutants were obtained by SSRP method in which shoots are regenerated from leaves of variegated individuals primarily selected at aseptic culture stage. Besides, the thus obtained variegated character was stable and did not disappear. The varieties of the variegated mutants obtained by SSRP method were Pink Mini, Purple and Purple Mini. The only variety of the variegated mutants obtained by FSRP method was Blue Vein.

Example 2

Creation of Variegated Torenia

Conventional Selection Method: Stem and leaf sections from torenia Summer Wave variety were subjected to callus induction treatment for one week, and then irradiated with $^{14}N$ ion beams (5 Gray) or $^{20}Ne$ ion beams (10 Gray) at RARF. The stem and leaf section calli after the irradiation were cultured on MS agar medium containing 1 mg/L BA for one to three months to allow shoot formation. The regenerated shoots were subjected to rooting under acclimatization conditions and then grown in greenhouse or the like. Subsequently, variegated plants were selected.

FSRP Method: Stem and leaf sections from torenia Summer Wave variety were subjected to callus induction treatment for one week, and then irradiated with 14N ion beams (5 Gray) or $^{20}Ne$ ion beams (10 Gray) at RARF. The stem and leaf section calluses after the irradiation were cultured on MS agar medium containing 1 mg/L BA for one to three months to allow shoot formation. The appearances of the formed shoots were observed, and the frequencies of variegated plants were examined. Since a large number of regenerated shoots were formed from one explant, those calli in which both albino (white) shoots and green shoots are present in mixture were selected. Subsequently, healthy variegated shoots independent from the explant were selected and acclimatized.

TABLE 4

|  | No irradiation | $^{14}N$-ion beams | $^{20}Ne$-ion beams |
| --- | --- | --- | --- |
| Frequency of Variegated Plants | 1.8% | 5.1% | 5.0% |
| No. of Acclimatized Shoots/One explant | 7 shoots | 10 shoots | 10 shoots |

Frequency of variegated plants: Variegated plants/Regenerated plants

As shown in Table 4, variegated plants appeared at a high frequency when either of the two kinds of heavy-ion beams was used. However, these variegated shoots were not stable in their chimeric characters. Chimeric characters disappeared afterward, and they turned into green or albino plants. However, a variegated plant was matured in one regenerated shoot.

The numbers of variegated mutants obtained by the conventional selection method and FSRP method, respectively, are shown in Table 5.

TABLE 5

|  | No irradiation | $^{14}N$-ion beams | $^{20}Ne$-ion beams | Total |
| --- | --- | --- | --- | --- |
| Conventional Selection Method | 0 | 0 | 0 | 0 |
| FSRP Method | 0 | 1 | 0 | 1 |

As shown in Table 5, no variegated mutants were obtained in the conventional method in which variegated plants are selected in greenhouse. In contrast with this, a variegated mutant was obtained by FSRP method in which plants are selected from regenerated plants from heavy ion irradiated calli. Besides, the thus obtained variegated character was stable and did not disappear.

The present specification includes the contents described in the specification of Japanese Patent Application No. 2002-993 based on which the present application claims priority. Also, all publications, patents and patent applications cited herein are incorporated herein by reference in their entity.

INDUSTRIAL APPLICABILITY

The present invention provides a method of creating chimeric plants efficiently. Since chimeric plants, such as variegated plants, have higher commercial value as garden crops than ordinary varieties, the method of creating such varieties efficiently is very useful in the field of agriculture.

The invention claimed is:

1. A method of creating a chimeric plant comprising:
   irradiating a plant stem explant with heavy-ion beams;
   allowing the formation of shoots from the plant stem explant irradiated with heavy-ion beams;
   selecting chimeric shoots from the formed shoots at the aseptic culture stage;
   collecting leaf explants from the selected shoots;
   allowing the regeneration of the collected leaf explants and the formation of shoots therefrom;
   selecting chimeric shoots from the resultant regenerated shoots at the aseptic culture stage; and
   growing the selected shoots and obtaining mature plants.

2. The method according to claim 1, wherein the chimeric shoots are variegated shoots.

3. The method according to claim 1, wherein the explant is a section including a portion which can grow into a bud.

4. The method according to claim 1, wherein the heavy-ion beams are C ion beams, N ion beams or Ne ion beams.

5. The method according to claim 1, wherein the plant is petunia.

* * * * *